United States Patent [19]

Jurgutis

[11] Patent Number: 4,728,335
[45] Date of Patent: Mar. 1, 1988

[54] HIP PROSTHESIS

[76] Inventor: John A. Jurgutis, 1304 15th St., Suite 405, Santa Monica, Calif. 90404

[21] Appl. No.: 941,599

[22] Filed: Dec. 15, 1986

[51] Int. Cl.4 .............................................. A61F 2/32
[52] U.S. Cl. ........................................ 623/23; 623/16
[58] Field of Search .................................... 623/16-23

[56] References Cited

U.S. PATENT DOCUMENTS

| | | | |
|---|---|---|---|
| 3,986,212 | 10/1976 | Sauer | 623/18 |
| 4,011,602 | 3/1977 | Rybicki et al. | 623/18 |
| 4,038,703 | 8/1977 | Bokros | 623/18 |
| 4,052,754 | 10/1977 | Homsy | 623/18 |
| 4,141,088 | 2/1979 | Treace | 623/22 |
| 4,164,794 | 8/1979 | Spector et al. | 623/18 |
| 4,168,326 | 9/1979 | Broemer et al. | 623/18 |
| 4,177,524 | 12/1979 | Grell et al. | 623/18 |
| 4,206,516 | 6/1980 | Pilliar | 623/18 |
| 4,234,972 | 11/1980 | Hench et al. | 623/18 |
| 4,272,855 | 6/1981 | Frey | 623/18 |
| 4,307,472 | 12/1981 | Morris | 623/18 |
| 4,309,488 | 1/1982 | Heide et al. | 623/18 |
| 4,351,069 | 9/1982 | Ballintyn et al. | 623/18 |
| 4,355,428 | 10/1982 | Deloison et al. | 623/18 |
| 4,385,405 | 5/1983 | Teinturier | 623/18 |
| 4,430,760 | 2/1984 | Smestad | 623/18 |
| 4,430,761 | 2/1984 | Niederer et al. | 623/18 |
| 4,549,319 | 10/1985 | Meyer | 623/18 |

FOREIGN PATENT DOCUMENTS 2153233  8/1985  United Kingdom ................. 623/16

Primary Examiner—Richard J. Apley
Assistant Examiner—David J. Isabella
Attorney, Agent, or Firm—Kelly, Bauersfeld & Lowry

[57] ABSTRACT

A hip prosthesis includes a femoral component with an elongated stem for seating within an elongated, longitudinally split sleeve having an exterior porous ingrowth surface. When implanted as a unit into the medullary canal, the femoral component stem wedges tightly into the sleeve to correspondingly press the sleeve into intimate and tight fit engagement with the bone. During normal postoperative use, any bone subsidence is accompanied by further wedging of the femoral component stem into the sleeve for maintenance of a secure mechanical interlock between the bone and prosthesis. However, in the event of failure for any reason, the femoral component and split sleeve are removable relatively easily to permit hip reconstruction with a new prosthesis.

12 Claims, 4 Drawing Figures

HIP PROSTHESIS

BACKGROUND OF THE INVENTION

This invention relates generally to improvements in prosthetic devices, particularly such as hip prostheses and the like. More particularly, this invention relates to an improved hip prosthesis designed for improved noncemented fixation with patient bone, while permitting relatively easy removal of the prosthesis, if required.

Artificial or prosthetic devices for implantation into animals, particularly humans, have been the subject of extensive research and development efforts for many years. Such prosthetic devices have typically comprised one or more implant components formed from a relatively biostable material having selected structural properties and unique shapes to replace all or part of selected bone structures, such as an anatomical joint including, for example, a hip or knee joint. The implant components are installed by surgical access to the subject bone or joint region and by resection of one or more bone surfaces to accommodate direct implant component attachment thereto. In the past, this bone attachment has been commonly achieved by use of bone cements, such as a methyl methacrylate based cement or the like, with the cement interdigitating within the interstices of bone surfaces to achieve mechanical fixation at the bone-cement interface.

In recent years a variety of potential disadvantages or limitations have been recognized with respect to cemented fixation of prosthetic devices. More particularly, it has been generally recognized that the use of bone cement to fixate implant components provides a temporary securement which normally requires significant restrictions upon postoperative patient activity to avoid failure of the cemented interface during the patient's lifetime. Failure of the cemented interface is especially undesirable, since the bone cement contributes to a significant degree of localized bone structure loss which makes implantation of a secondary replacement prosthesis extremely difficult and frequently impossible. The problems encountered by use of cemented prosthetic devices are particularly severe with high load bearing, highly stressed joints, such as a hip joint.

In an effort to avoid use of bone cements, a variety of improved prosthetic devices have been proposed for noncemented attachment to resected bone surfaces. Some of these noncemented devices have suggested the use of attachment surfaces having closely control porosity characteristics designed to accommodate direct bone attachment by ingrowth or resorption of living cancellous bone or tissue. However, while these bone ingrowth proposals appear to offer significant advantages over prior cemented designs, various problems have still been encountered with respect to insuring a positive and stable prosthesis fixation particularly at highly loaded and stressed joints, such as the hip. For example, slight subsidence of the prosthesis-supporting bone during normal postoperative patient function can result in permanent loosening and eventual failure of the prosthesis. However, subsequent surgical removal of the failed prosthesis can be extremely difficult and/or impossible.

There exists, therefore, a significant need for an improved prosthetic device particularly adapted for use as a hip joint, wherein the prosthesis is designed for noncemented fixation to patient bone and to withstand high loading and stress to provide a prolonged service life. In addition, in the event of prosthesis failure for any reason, there exists a need for an improved prosthesis which can be removed relatively easily for replacement with an appropriately sized secondary prosthesis. The present invention fulfills these need and provides further related advantages.

SUMMARY OF THE INVENTION

In accordance with the invention, an improved implantable prosthesis device is provided for secure, noncemented fixation with respect to patient bone. The improved prosthesis is particularly adapted for use as a hip prosthesis and is designed to mechanically interlock in a secure and stable manner within the medullary canal of a patient's femur, with a wedging action which increases upon slight bone subsidence during normal postoperative patient function. However, in the event of prosthesis failure for any reason, the improved prosthesis of the present invention is advantageously designed for facilitated surgical removal and replacement.

In a preferred form of the invention, the improved hip prosthesis comprises a rigid femoral component having a elongated lower stem joined to an upper neck and head, with the head being adapted to seat rotatably within an appropriate acetabular component. The femoral stem has an upper cross sectional shape of generally elliptical configuration which blends gradually into a narrower, lower cross sectional shape of approximately circular configuration and extending along a centerline roughly approximating the shape of the femoral medullary canal. The specific cross sectional shape of the femoral stem is chosen to seat within an elongated, longitudinally split sleeve having, in the preferred, form an external porous ingrowth surface. The interior surface geometry of the sleeve is chosen for close conformance with the cross sectional shape of the femoral stem, whereas the external sleeve geometry is configured for relatively close, intimate engagement with patient bone lining the femoral medullary canal.

In use the femoral component and the elongated sleeve are implanted into the resected femur of a patient with the femoral stem and sleeve seated together within the medullary canal. The femoral stem thus wedges downwardly into the elongated sleeve which is wedged in turn tightly against patient bone lining the medullary canal. This wedging action is enhanced during normal postoperative patient function to increase the tight mechanical interlock between the sleeve and bone, especially in the event of slight bone subsidence over a period of time. However, in the event of prosthesis failure for any reason, the femoral component can be withdrawn relatively easily from the elongated sleeve which is then sufficiently exposed for relatively easy removal and replacement with an appropriate secondary prosthesis.

Other features and advantages of the invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 1:
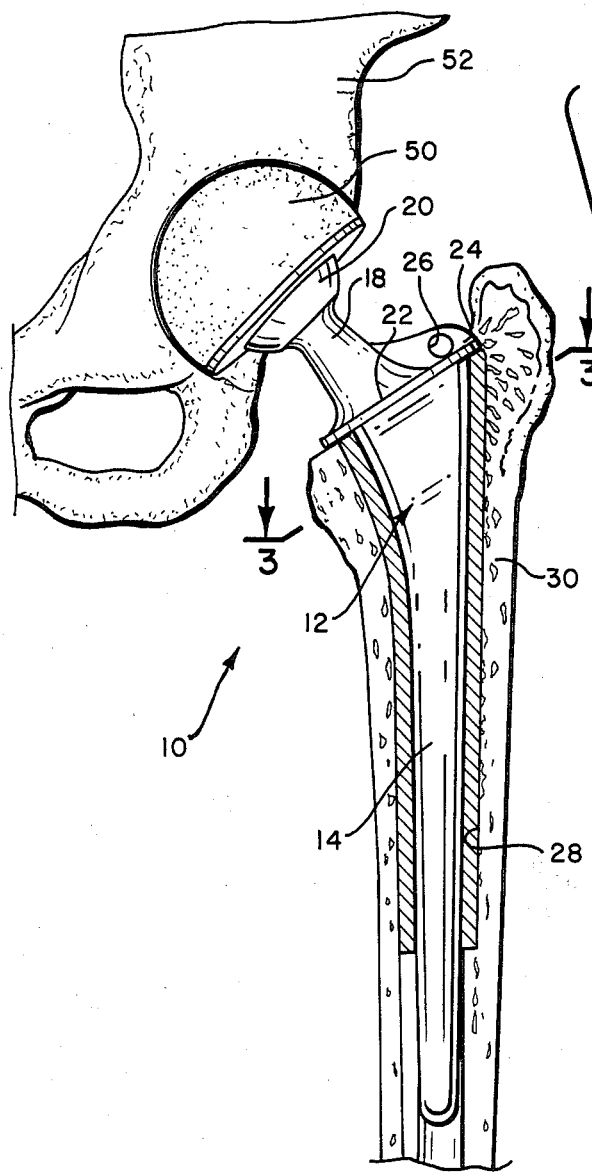
FIG. 1 is a fragmented elevation view illustrating an implanted hip prosthesis embodyng the novel features of the invention, with portions thereof depicted in vertical section to illustrate prosthesis fixation within the femur of a patient.
Figure 2:
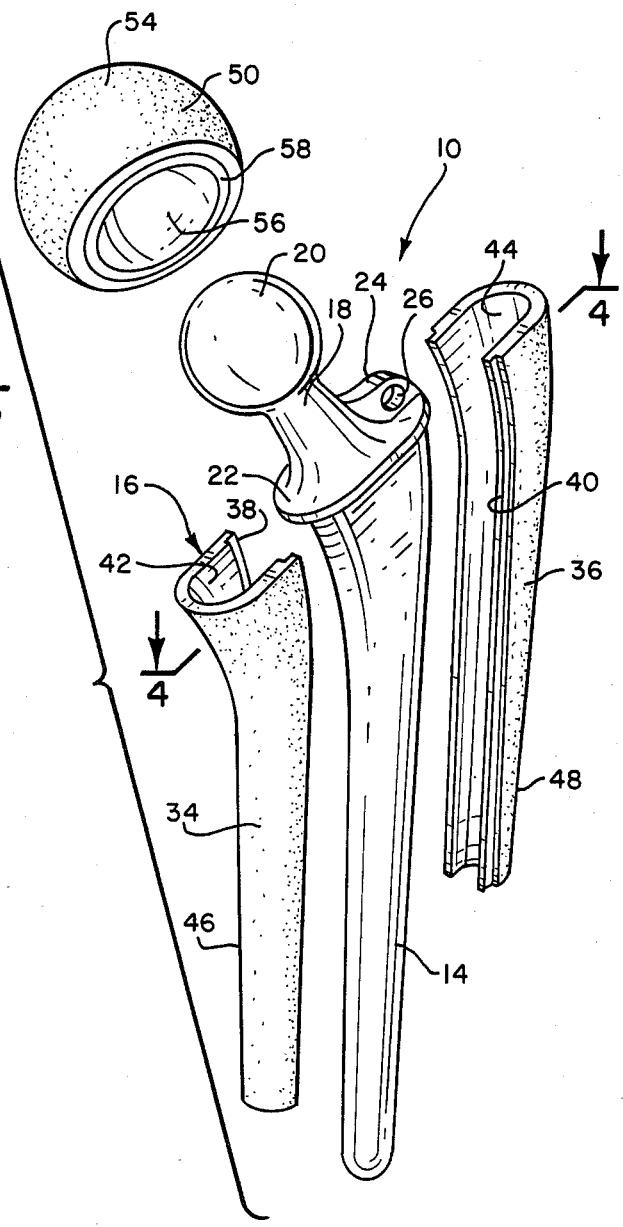
FIG. 2 is an exploded perspective view illustrating the components forming the hip prosthesis of FIG. 1.

As shown in the exemplary drawings, an improved prosthetic device in the form of a hip prosthesis is referred to generally by the reference numeral 10 in FIGS. 1 and 2. The hip prosthesis 10 includes a femoral component 12 having an elongated lower stem 14 in combination with an elongated, longitudinally split sleeve 16. In use, the sleeve 16 is wedged tightly by the femoral stem 14 into intimate and secure mechanical interlock engagement with patient bone.

The improved prosthesis of the present invention beneficially provides a relatively simple combination of components which can be implanted quickly and easily into resected patient bone and securely anchored in place without requiring fixating cements. The invention is particularly suited for use at relatively high load bearing and high stress joints, such as the hip, wherein normal postoperative patient function frequently results in at least some bone subsidence at the contact interface with the prosthesis. In accordance with one feature of the invention, such bone subsidence is accompanied by further or increased wedging of the prosthesis into the medullary canal of the bone to maintain a tight mechanical interlock between the bone and the prosthesis. However, in the event of prosthesis failure for any reason, the improved prosthetic device of the present invention is further adapted for facilitated removal and replacement with an appropriate secondary prosthesis.

As shown in FIGS. 1 and 2, the illustrative hip prosthesis 10 comprises the lower stem 14 joined at its upper end to an upwardly extending and angularly set neck 18 which in turn carries an upper ball-shaped head 20. A slightly enlarged platform 22 is formed generally at the juncture between the stem 14 and neck 18, and a raised rib 24 may also be provided on the upper side of this platform 22 to include a transverse opening 26 for reception of appropriate surgical instruments to facilitate prosthesis implantation and/or extraction, as will be described in more detail. The entire femoral component 12 is normally constructed from a rigid metal alloy chosen for high strength and prolonged service life together with biostable compatibility upon implantation.

The cross sectional shape of the femoral stem 14 is chosen to roughly approximate the anatomical configuration of the medullary canal 28 (FIG. 1) over the upper region of a patient's femur 30. More specifically, as shown, the femoral stem 14 has a generally elliptical cross sectional shape at the upper end beneath the platform 22. From this upper end, the stem 14 extends downwardly with a gradually decreasing major axis dimension and a centerline which curves through an appropriate angle to blend with a lower, generally straight region which approaches a substantially circular cross sectional shape at the lower end of the stem 14. This geometry generally approximates the internal configuration of the bone surface lining the femoral medullary canal 28, yet permits femoral component manufacture without specific reproduction of the various anatomical complexities of the femur geometry, such as slight posterior bow of the femur, etc.

Figure 3:
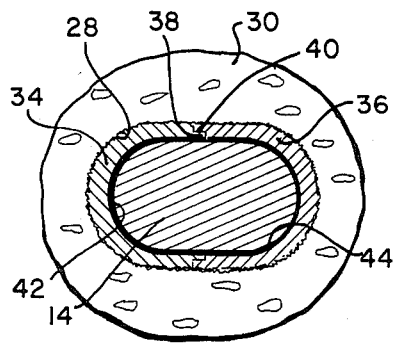
FIG. 3 is an enlarged sectional view taken generally on the line 3—3 of FIG. 1.
Figure 4:
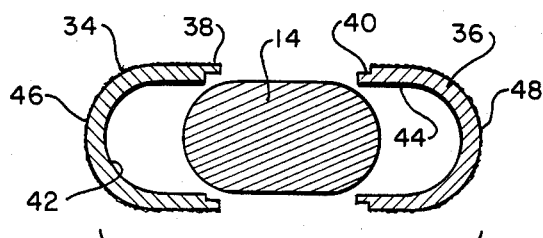
FIG. 4 is an enlarged sectional view taken generally on the line 4—4 of FIG. 2.

The overall geometry of the femoral stem 14 is sized and shaped to seat with a wedging action into the longitudinally split sleeve 16. In the preferred form, this sleeve 16 comprises mating sleeve halves 34 and 36 formed from a substantially rigid material such as a cast composite material or the like selected for stable seating between the femoral stem 14 and the bone surface lining the medullary canal 28. As shown in FIGS. 2-4, the sleeve halves 34 and 36 include mating lips 38 and 40, respectively, along the facing side margins for at least partially overlapping one another when the sleeve halves are assembled about the femoral stem 14. Inner surfaces 42 and 44 of the sleeve halves cooperate, when the sleeve halves are assembled about the stem 14, to define an elongated channel of closed cross sectional shape for close, substantially mating engagement with the external surface configuration of the stem 14. Accordingly, these inner surfaces 42 and 44 of the sleeve halves cooperatively define an upper generally elliptical shape which decreases in a downward direction in major axis diameter and then curves to blend with a lower and generally straight section terminating in a lower end of generally circular shape. As shown in FIG. 1, the lower margin of the sleeves halves 34 and 36 may terminate above the lower end of the stem 14, although the sleeve halves will normally extend over at least the upper two thirds of the stem length.

The outer surfaces 46 and 48 of the sleeve halves 34 and 36 are geometrically shaped to conform with the anatomical geometry of bone surface lining the medullary canal 28 of the femur 30. In this regard, anatomical complexities normally present in the femoral geometry may be imparted to the outer surfaces 46 and 48 to insure a closely conforming and intimate surface contact engagement between the sleeve 16 and the patient bone. In the preferred form, these outer surfaces 46 and 48 of the sleeve halves are defined by porous surfaces of closely controlled porosity, such as an array of titanium or cobalt chrome spherical beads or titanium mesh or other known porous surface substances designed for bone and/or tissue ingrowth and/or resorption. Alternately, if desired, the sleeve halves can be constructed in their entireties for the porous ingrowth material.

The hip prosthesis 10 is implanted by appropriate surgical access of the hip joint of a patient, all in a manner known to those skilled in the art. More particularly, by way of general description, the access hip joint is dislocated to permit resection of the femoral head and neck followed by sufficient removal of cancellous bone at the upper end of the femur to expose the underlying medullary canal 28. The medullary canal is appropriately broached to permit implantation of the femoral component stem 14 and the split sleeve 16 as a unit. The femoral stem 14 is thus seated within and wedged downwardly against the inner surfaces 42 and 44 of the sleeve halves 34 and 36, resulting in outward pressing of the sleeve half outer surfaces 46 and 48 into intimate surface contact engagement with the bone surface lining the medullary canal 28. During such implantation, the underside of the femoral component platform 22 is normally spaced a short distance such as one or two millimeters above the upper edges of the sleeve halves 34 and 36.

The implantation procedure normally also includes implantation of an acetabular or socket component 50 into the patient hip bone 52, as viewed in FIG. 1. This acetabular component 50 may also include an upper, generally hemispherical surface 54 having controlled porosity for bone and/or tissue ingrowth. The underside of the acetabular component 50 defines an open socket 56 which is normally lined with an appropriate bearing component 58 and seatingly receives the ball-shaped head 20 of the femoral component 12.

In use, normal postoperative functional loading of the hip joint tends to enhance the wedging action of the femoral component stem 14 downwardly into the sleeve 16, thereby further enhancing the intimate pressing engagement of the sleeve against the bone lining the medullary canal. This tight pressing engagement enhances bone and/or tissue ingrowth for resorption into the porous ingrowth surfaces of the sleeve, thereby further enhancing overall mechanical fixation of the prosthesis. In this regard, at least some bone subsidence is normally anticipated and is accompanied by slight downward advancement of the stem 14 into the sleeve 16 to offset any loosening effect which would otherwise occur. The sleeve 16 is thus maintained tightly against the adjacent bone surfaces for secure and stable prosthesis fixation. Downward stem motion is limited by eventual seated contact of the platform 22 against the upper margins of the sleeve halves 34 and 36 and the upper resected surface of the femur proximal end.

In the event of prosthesis failure for any reason, such as failure of bone and/or prosthesis structures, the hip prosthesis 10 of the present invention can be surgically exposed and removed without significant risk of further damage to the patient. In particular, the wedged interlock between the femoral stem 14 and the sleeve 16 permits relatively easy femoral component extraction which is facilitated by engagement of appropriate tools within the transverse opening 26 on the rib 24. Once the femoral component 12 is extracted, sufficient space is present in and around the upper end of the sleeve 16 to permit relatively easy sleeve extraction, if required. In this regard, the split nature of the sleeve accommodates sufficient sleeve manipulation within the medullary canal 28 to loosen and extract the sleeve in an expedited manner.

The improved hip prosthesis 10 of the present invention thus provides a relatively simple yet highly stable prosthetic device for enhanced fixation without requiring use of bone cements and the like. The wedging interlock between the femoral component 12 and the sleeve 16 permits manufacture of a relatively small number of different femoral component sizes in combination with a relatively small number of sleeve sizes to fit the anatomical requirements of a wide range of patients. Various femoral component and sleeve sizes may be interchanged to closely match the physiological shape of a patient, without requiring manufacture of many different component sizes.

A variety of further modifications and improvements to the hip prosthesis of the present invention will be apparent to those skilled in the art. Accordingly, no limitation on the invention is intended by the way of the description herein, except as set forth in the appended claims.

What is claimed is:

1. A hip prosthesis for implantation into the medullary canal of a resected femur, said prosthesis comprising:

an elongated and substantially rigid femoral component having a head and an elongated stem; and
   an elongated, longitudinally split sleeve including a pair of sleeve halves with mating side margins having at least partially overlapping mating lips to define an elongated channel of closed cross sectional shape;
   said femoral component stem being received into said split sleeve channel and said stem and sleeve being receivable as a unit into the medullary canal of the resected femur, whereby normal postoperative patient function wedges said stem tightly into said sleeve to wedge said sleeve into tight intimate contact with the bone surface lining the medullary canal.

2. The hip prosthesis of claim 1 wherein said split sleeve has at least a substantial portion of the exterior surface thereof defined by a porous ingrowth material.

3. The hip prosthesis of claim 1 wherein said femoral component stem has a cross sectional geometry of progressively diminishing size for the upper end to the lower end thereof.

4. The hip prosthesis of claim 3 wherein the cross sectional geometry of said femoral component stem fits substantially matingly into said split sleeve channel.

5. The hip prosthesis of claim 4 wherein the exterior geometry of said split sleeve is formed to fit in close, intimate contact with the bone surface lining the medullary canal.

6. The hip prosthesis of claim 1 including an enlarged platform formed on said femoral component generally at the upper end of said stem and below said head.

7. A hip prosthesis for implantation into the medullary canal of a resected femur, said prosthesis comprising:

an elongated and substantially rigid femoral component having an upper head, an elongated lower stem, and a short neck joined between said head and stem;
   said femoral component stem having a generally elliptical cross section shape generally at the upper end thereof and extending downwardly therefrom generally along a curved centerline approximating the centerline of the medullary canal with a progressively diminishing major axis to a lower stem end of substantially circular cross section; and
   an elongated, longitudinally split sleeve formed from a pair of sleeve halves with mating side margins including at least partially overlapping mating lips to define an elongated channel of closed cross sectional shape for close reception of said femoral component stem downwardly into said channel with a wedging action;
   said sleeve halves being receivable into the medullary canal of the resected femur and said femoral component stem being receivable downwardly into said sleeve with a wedging action to urge the exterior surfaces of said sleeve into intimate surface engagement with the bone lining the medullary canal.

8. The hip prosthesis of claim 7 wherein said split sleeve has at least a substantial portion of the exterior surface thereof defined by a porous ingrowth material.

9. The hip prosthesis of claim 7 wherein the exterior surfaces of said sleeve are formed generally for conformance with the shape of the bone lining the medullary canal.

10. A prosthesis for implantation into the medullary canal of a resected bone, said prosthesis comprising:

an elongated and substantially rigid prosthesis component having an elongated stem of diminishing cross sectional size from a proximal to distal end thereof; and an elongated and longitudinally split sleeve having a pair of sleeve halves with mating side margins including at least partially overlapping mating lips to define an elongated channel of closed cross sectional shape diminishing in size from a proximal to distal end thereof and an exterior surface geometry for close conformance with the bone lining the medullary canal;

said sleeve being receivable into said medullary canal and said stem being receivable into said sleeve channel with a wedging action to urge said sleeve tightly into intimate surface engagement with the bone lining the medullary canal.

11. The prosthesis of claim 10 wherein said split sleeve has at least a substantial portion of the exterior surface thereof defined by a porous ingrowth material.

12. The prosthesis of claim 1 wherein said split sleeve has a length to extend over at least two thirds of the length of said stem at the end of said stem adjacent said head.

* * * * *